(12) United States Patent
Schweigert

(10) Patent No.: US 8,501,430 B2
(45) Date of Patent: Aug. 6, 2013

(54) DETERMINATION OF BIOLOGICAL MATERIAL INGREDIENTS

(76) Inventor: Florian Schweigert, Berlin (DE)

( * ) Notice: Subject to any disclaimer, the term of this patent is extended or adjusted under 35 U.S.C. 154(b) by 700 days.

(21) Appl. No.: 12/310,897

(22) PCT Filed: Sep. 13, 2007

(86) PCT No.: PCT/EP2007/059664
§ 371 (c)(1),
(2), (4) Date: Nov. 12, 2009

(87) PCT Pub. No.: WO2008/031874
PCT Pub. Date: Mar. 20, 2008

(65) Prior Publication Data
US 2011/0256566 A1    Oct. 20, 2011

(30) Foreign Application Priority Data
Sep. 13, 2006  (DE) .......................... 10 2006 044 795

(51) Int. Cl.
*C12Q 1/44*  (2006.01)
*C12Q 1/34*  (2006.01)
*C12Q 1/61*  (2006.01)
*C12Q 1/60*  (2006.01)

(52) U.S. Cl.
USPC ...................... 435/19; 435/11; 435/18; 435/4

(58) Field of Classification Search
USPC ........................................................... 435/4
See application file for complete search history.

(56) References Cited

PUBLICATIONS

Ryan, John, et al; "Lipid Extraction from Blood and Biological Samples." Chemosphere, 34, 999-1009, 1997.*
Mege, S., et al; "Surfactant effects in vanadium alkoxide derived gels." Journal of Non-Crystalline Solids, 238, 37-44, 1998.*
van Os, Nico M.; Nonionic Surfactants Organic Chemistry. 1st Edition, CRC Press, 1997.*
Spiro, Michael, et al; "Kinetics of Solvent Extraction of Essential Oil from Rosemary Leaves." Flavour and Fragrance Journal, 9, 187-200, 2004.*
Lewis, Tom, et al; "Evaluation of extraction methods for recovery of fatty acids from lipid-producing microheterotrophs." Journal of Microbiological Methods, 43, 107-116, 2000.*
Abe, Akira, et al; "A Novel Enzyme That Catalyzes the Esterification of N-Acetylsphingosine." The Journal of Biological Chemistry, 271, 14383-14389, 1996.*
Parsons, Leon W.; "Progress on Emulsions." The Journal of Industrial and Engineering Chemistry, 14, 797-798, 1922.*
Markham, Jonathan E.; "Separation and Identification of Major Plant Sphingolipid Classes from Leaves." The Journal of Biological Chemistry, 281, 22684-22694, 2006.*
Chan, Vincent; "Effect of Hydrophobicity and Electrostatics on Adsorption and Surface Diffusion of DNA Oligonucleotides at Liquid/Solid Interfaces." Journal of Colloid and Interface Science, 203, 197-207, 1998.*
Maier, Clive, et al; Polypropylene: The Definitive User's Guide and Databook. Plastics Design Library, 1st Edition, 1999.*
Armarego, W. L. F.; et al; Purification of Laboratory Chemicals. Butterworth-Heinemann, 5th Edition, 2003.*
Hames, David; et al; Instant Notes in Biochemistry. Taylor & Francis, 3rd Edition, 2005.*

* cited by examiner

*Primary Examiner* — Blaine Lankford
*Assistant Examiner* — David Berke-Schlessel
(74) *Attorney, Agent, or Firm* — Wood, Phillips, Katz, Clark & Mortimer

(57) ABSTRACT

The invention relates to a method for analysing ingredients, in particular lipids and/or vitamins and biological material ingredients, to methods of using relevant organic solvents or organic solvent mixtures, and to a spectrophotometer for measuring biological material ingredients. It is proposed to treat the biological materials with at least one organic solvent which extracts the ingredients, to convert the bi ological materials to a solidified form during the extraction, with the result that a solidified sediment and a liquid organic phase as the supernatant are formed, and to examine the extracted ingredients in the supernatant.

23 Claims, 9 Drawing Sheets

|  | Pluronic 101 content | | | | |
| --- | --- | --- | --- | --- | --- |
|  | 0.1 % | 0.5 % | 1.0 % | 2.0 % | 3.0 % |
| Sample 1 (mg/L) | 2.84 ± 0.23 | 2.73 ± 0.32 | 3.19 ± 0.29 | 3.69 ± 0.31 | 3.59 ± 0.40 |
| Sample 2 (mg/L) | 1.38 ± 0.12 | 1.37 ± 0.19 | 2.20 ± 0.21 | 2.38 ± 0.24 | 2.43 ± 0.09 |

Fig. 4

DETERMINATION OF BIOLOGICAL MATERIAL INGREDIENTS

AREA OF APPLICATION AND PRIOR ART

The present invention relates to a method for analyzing ingredients, in particular lipids and/or vitamins, of biological materials with an enrichment of the ingredients from the biological materials, in which the biological materials are treated with at least one organic solvent which extracts the ingredients, to uses of organic solvents or organic solvent mixtures in this regard and to a spectrophotometer for measuring ingredients of biological materials.

Modern methods for analyzing biological materials often include steps for removal, extraction, isolation and/or enrichment of components and ingredients of the biological materials. Such method steps are indispensible both in qualitative and quantitative analysis for removing interfering or result-falsifying substances. In addition, so-called high-throughput methods or microfluidic systems which provide their entire functionality reduced to the size of a chip card are being generally adopted in the analytical sector. Such methods or systems are colloquially subsumed under terms such as vest pocket lab, lab-on-a-chip or point-of-care systems (diagnostic systems which can be used directly next to the patient). Substantial miniaturization is necessary for such a mode of analysis. The miniaturization of such systems entails a susceptibility to impurities which may block, and as a result make unusable, surfaces and capillary systems. Such systems or methods therefore often require laborious sample preparation with time-consuming and equipment-intensive intermediate steps before the final analysis. Such problems relate in particular to the analysis of blood or food products. The commonest investigations undertaken in human and veterinary medical laboratories are analyses of blood for diagnosis. Normally, the investigations are carried out on the cell-free portion of whole blood samples, especially on blood serum or blood plasma. Investigations on whole blood are only undertaken reluctantly because of a risk of lysis of blood cells, especially a risk of hemolysis of erythrocytes. Conventional techniques suitable for removing cellular components of blood before analysis are centrifugation and/or filtration. The removal of such corpuscular components serves to avoid possible interfering effects both from cells and from cell fragments, and from lysis products, especially in lab-on-a-chip analysis. Normally, even with lab-on-a-chip analysis the removal currently takes place conventionally by means of centrifugation or filtration steps. Filtration on the lab-on-a-chip is preferred for direct removal of the cells. The main problem arising in this connection is rapid blockage of capillaries, irrespective of the filter system used in each case. For this reason, only volumes of a few microliters can usually be applied as limiting amount. Similar problems also relate to the analysis of food products.

The necessary removal by centrifugation or filtration leads to an increased time taken, and an increased requirement for reagents, equipment and biological materials, especially blood, for the analysis. There is thus a great need for methods for analyzing ingredients of biological materials, especially blood, which can be carried out with unfiltered or uncentrifuged samples.

PROBLEM AND SOLUTION

A problem addressed by the present invention is therefore to provide a method for analyzing ingredients of biological materials which dispenses with centrifugation or filtration of samples of the biological materials before the analysis thereof, and to provide an apparatus for analysis of ingredients obtained by the method.

The present invention solves the technical problem underlying it by the method mentioned at the outset for analyzing ingredients, especially lipids and/or vitamins, of biological materials with an enrichment of the ingredients from the biological materials, in which the biological materials are treated with at least one organic solvent which extracts the ingredients, with the biological materials being converted in the extraction into a consolidated form so that a consolidated sediment and a supernatant of liquid organic phase are formed, and the ingredients extracted into the supernatant are investigated.

In the context of the present invention, "biological materials" are intended to mean materials obtained from plants, animals, humans and/or microorganisms, especially endogenous materials, preferably samples of endogenous materials.

"Microorganisms" are intended to comprise in the context of the present invention besides, for example, eukaryotes such as algae, prokaryotes and/or fungi, such as yeasts, also viruses. It is particularly intended that "biological materials" comprise organisms obtained from culture, and culture supernatants.

The biological materials are provided in the method of the invention by employing samples of the biological materials, preferably samples taken from humans or animal organisms. It is also possible expediently to use discharged or secreted biological materials. Furthermore, it is also possible to cultivate the biological materials before use thereof in the method of the invention, especially outside the human or animal body.

A "consolidation" is intended to mean in the context of the present invention an increase in viscosity, especially an increase in viscosity of the biological materials, so that a consolidated sediment is formed. It is also possible moreover to reach a viscosity which is between that of a liquid and that of a solid. It is particularly intended by this to mean consolidated forms or consolidated sediments of the biological materials of the nature of ointments, creams, fillings of gel saddles for cyclists, hair gels for shaping hair styles, preferably gels of the nature of gelatin, jelly or gelatinous material. The consolidation can be achieved for example by precipitation or resinification, especially by treatment with acids or resin-containing compositions.

Suitable according to the invention as consolidated form or consolidation are gels or gelatinous states. It is relatively easy to describe the gels or gelatinous states from the technical viewpoint. However, a generally accepted comprehensive definition of gels is still sought.

Gels are normally described as colloidal systems composed of at least one solid phase and one liquid phase. The solid phase in some gels may be in the form of a sponge-like, three-dimensional network in which the liquid phase is included. In terms of their mechanical properties, gels are in a solid-like state. Such a state is distinguished by components distributed uniformly in the complete system. The gels may be characterized both by uniform structures, especially ordered structures, and by unordered structures, especially in the case of networks of aggregated polymers. The gels can moreover be characterized according to the physical and chemical nature of their binding forces and of their liquid phases. Where aqueous media constitute the liquid phase, the gel is referred to as "hydrogel". In the case of organic media, the gel is referred to as "organogel". Gels including surface-active substances as liquid phase are referred to as "amphiphilogel".

A gel is normally produced by dissolving a gelator in a heated solvent. Gelation of the solution starts on cooling. Gel formation starts when the solubility of the gelator or the gelling agent in the solvent is reduced. This leads to a clustering of gelator molecules (self-aggregation). Parts of the solvent are bound in the gelator. As a result, the solvent is consolidated in its volume, in particular its whole volume, and it can bear its own weight.

Suitable gelators or gelling agents are various low molecular weight substances, depending on the nature of the gels. Numerous molecules which form hydrogels in aqueous solutions are to be found in nature. Gelling agents which, especially as additives in food products, bind water or swell in water, i.e. lead to a gelation, and which should be mentioned are in particular agar-agar, alginic acid, carrageenan, gelatin, guar gum, gum arabic, locust bean gum, pectin, especially amidated pectin, and modified starch.

Examples of gelators for organogels which should be mentioned are fatty acids, fatty acid derivatives, especially metal salts of fatty acids, steroid derivatives, especially cholesterol derivatives, amino acid-containing gelators, aromatic gelators, especially anthraquinone derivatives, for example antryl derivatives, calixarenes, pyridines, as well as sorbitol derivatives, and polyol derivatives. A well-known organogel is formed by lecithin.

Also suitable for the consolidation of the biological samples besides the gel formation are further techniques known to the person skilled in the art.

The method according to the present invention is intended for the analysis of ingredients, preferably lipids and/or vitamins and biological materials. The method serves in particular to extract lipophilic ingredients. The biological materials are treated with organic solvents into which the ingredients are transferred during the extraction. The biological materials are preferably present in the aqueous medium.

The biological materials are surprisingly converted into a consolidated form during the extraction by the method of the invention. A treatment with organic solvents, especially solvent mixtures, results in formation of a multiphase system, in particular a system consisting of two phases. While the consolidation is progressing, preferably simultaneously, the biological materials, especially samples of the biological materials, are extracted.

The biological materials can be treated with the solvents in such a way that the biological materials are added to the solvents, but it is also possible to add the solvents to the biological materials.

The consolidation of the biological materials results in the solvents intended for the extraction being separated from the biological materials. A consolidated sediment and a supernatant is formed. The supernatant comprises the solvents intended for the extraction, and the ingredients, especially lipophilic ingredients, which have been transferred into the organic solvents.

The biological materials are thus advantageously separated through the consolidated form from the extracted ingredients present in the supernatant. The biological materials form the consolidated sediment, and the ingredients are located in the organic solvent above it and can subsequently be investigated by known analytical techniques.

Possible Mechanism Of Action

Mixing of the biological materials, for example blood, with the organic solvents employed in the method of the invention, for example in the form of solvent mixtures of polar and nonpolar solvents, leads to a phase separation. The polar solvent essentially, in accordance with its partition coefficient, enters the biological material which represents an aqueous phase. Since ingredients, preferably lipophilic ingredients, for example in the form of membrane components and lipoproteins, are present in the aqueous phase, the polar solvent is enriched in these structures. The polar solvents are able to penetrate into cell membranes, such as, for example, the cell membrane of the erythrocytes in whole blood, and interact with the lipid portion. Two effects occur: highly lipophilic ingredients are dissolved out of their integrated system and can be extracted into the supernatant. The polar solvent interacts with less lipophilic ingredients in the cell membranes or lipid-containing structures. Suitable lipids for the effects leading to gel formation are the phospholipids occurring in cell walls and lipoproteins. Biological membranes include a large number of phospholipids differing in chemical composition.

An interaction with the phospholipids and a removal of cholesterol from the cell membrane leads to a cross linking of the cell membranes (interdigitation) and to the gel formation. A presence of cholesterol enhances a fluid behavior (fluidity) of the cell membrane through formation of a so-called $L_o$ phase ("liquid-ordered") and prevents the cross linking. As the cholesterol content in model membranes increases there is a reduction in the membrane cross linking by polar organic solvents such as alcohols (methanol, ethanol, propanol, butanol). To achieve comparable effects when there is cholesterol enrichment, higher alcohol concentrations are necessary. Surface-active substances in sublytic concentrations and various short-chain alcohols also lead to a depletion of cholesterol from membranes. The possibility of alcohols interacting with the membrane-associated phospholipids is also supported by observations that alcohols extract cholesterol rather than phospholipids. The extractability of phospholipids is generally worse.

Clear solutions are formed as supernatants advantageously by the method of the invention and can be subjected to further analysis, preferably without further treatments. The solvents or solvent mixtures preferably used have a lower specific density than water. It is thus ensured that a liquid supernatant is formed. It may besides this be expedient to use solvents with a higher density than water in order to achieve creaming of the consolidated biological materials. This may, especially depending on the sample vessel used, be advantageous for further spectroscopic investigations. Solvents with a lower specific density than water are preferably employed in the method of the invention.

The biological materials used in the method of the invention preferably show the desired consolidation while the method is carried out. It is also possible to carry out a treatment with substances which bring about the desired consolidation. It is possible in particular to use the gelators or gelling agents previously mentioned.

In a further embodiment, the biological materials include plant, animal, human and/or microbial materials which are derived in particular from cell cultures.

It is possible according to the invention to use all biological materials which can be subjected to extraction.

In a further preferred embodiment of the method, the biological materials are subjected before use thereof to pretreatments, especially purification processes.

Examples of suitable pretreatments are pulpings. Suitable pulpings are treatments with homogenizers. Homogenizers which should be mentioned are for example cutters, Ultraturrax equipment, mills etc. The biological materials are subjected thereby to a reduction in size in order to increase their surface area. The reduction in size increases the efficiency of extraction. Besides this, treatments with low temperature, in particular with liquid nitrogen, are also suitable. The pulpings serve to release, and thus make available to extraction, ingredients from the biological materials. The biological materials can also be subjected as pretreatment to a removal of impurities and/or interfering substances, in particular washing processes, for example with buffer solutions.

In a further preferred embodiment of the method, tissues, organs and/or body fluids are used as biological materials.

The biological materials preferably used are those employed in the medical sector for diagnosis and/or monitoring of therapy.

In a further preferred embodiment of the method, the body fluids used are blood, plasma, serum, urine, amniotic fluid, uterine fluid, follicular fluid, synovia, sperm, pulmonary fluid and/or secretions.

The secretions are preferably milk, sweat, tear fluid, saliva and/or gastrointestinal tract secretions, especially bile fluids and/or pancreatic secretion. It is possible according to the invention to use blood, preferably whole blood, as body fluid. Blood is preferably used as biological material in the method of the invention. As pretreatment, the blood is preferably treated with anticoagulant substances, especially with polyanionic polysaccharides, preferably with heparin and/or heparinoids. It is further possible to employ as anticoagulants antithrombin III, especially in the form of heparin-antithrombin complexes. Exogenous anti-coagulants can also be employed in addition. Suitable exogenous anticoagulants are in particular vitamin K antagonists or calcium complexing agents. Coumarins should be mentioned in particular as vitamin K antagonists, and citrate, oxalate, preferably ethylenediaminetetraacetate (EDTA) should be mentioned in particular as calcium complexing agents.

Hemolysis of the blood, especially of the blood cells, is advantageously avoided by the method of the invention. The consolidation according to the invention of the blood leads to the blood cells being embedded in a gelatinous environment and thus protected from hemolysis.

It is further advantageous that the extraction is carried out manually by shaking, in particular cautious shaking avoiding hemolysis. It is also possible to employ aids for extracting the blood with the solvents, in particular vibrating tables, rocking equipment, vertical rotators, magnetic stirrers and other stirring techniques. Manual mixing has the advantage of being able to undertake the extraction independently of a source of current or electrical equipment.

In a further preferred embodiment of the method, food products of animal and/or vegetable origin, especially homogenates of food products, are employed as biological materials.

Suitable food products are in particular eggs, preferably whole egg yolk, fruit, vegetables, especially carrots, and/or fish and/or meat. Besides these, the method of the invention can be used to investigate as food products juices, especially fruit and/or vegetable juices, preferably carrot juices.

The food products preferably suitable for the method of the invention are those including ingredients which are essential for the human diet, preferably lipophilic ingredients.

In a further preferred embodiment of the method, polarly protic solvents are used as organic solvents, especially alcohols.

In a further preferred embodiment of the method, the polarly protic solvents are selected from the group comprising methanol, ethanol, 1-propanol, 2-propanol (isopropanol), butanol, pentanol, hexanol and mixtures thereof.

The use of alcohols in the method of the invention surprisingly brings about the consolidation of the biological samples. Mixtures of ethanol and 2-propanol (isopropanol) are preferably used.

In a further preferred embodiment of the method, at least one polarly aprotic solvent is used as organic solvent, and esters in particular are used, preferably ethyl acetate.

Besides the preferred polarly protic solvents it is also advantageously possible to employ in the method of the invention polarly aprotic solvents.

In a further embodiment of the method, nitriles, preferably acetonitrile, are used as polarly aprotic solvents.

In a further embodiment of the method, ketones, preferably acetone, are used as polarly aprotic solvents.

In a further embodiment of the method, dimethyl sulfoxide and/or N,N-dimethylformamide are used as polarly aprotic solvents.

In a further embodiment of the method, ethers, especially diethyl ether, are used as polarly aprotic solvents.

The solvents mentioned hitherto serve to consolidate the biological materials. The polar solvents are preferably employed in the form of mixtures depending on the biological materials.

In a further preferred embodiment of the method, at least one nonpolar solvent, in particular alkanes, preferably C5- to C12-alkanes, are used as solvents.

In a further preferred embodiment of the method, hexane, heptane and/or octane, in particular isooctane, are used as nonpolar solvents.

In a further embodiment of the method, aromatic compounds, especially toluene and/or benzene, are used as nonpolar solvents.

Said nonpolar solvents serve in the method of the invention as extractants for the ingredients, in particular for the lipophilic ingredients.

It may be expedient according to the invention to use derivatives or isomers of organic solvent molecules. The solvents may be anhydrous, hydrous, branched, unbranched, cyclic, acyclic, halogenated or unhalogenated.

A division into polar or nonpolar solvents can take place from various viewpoints in the art. For example, definitions of polarity or solvent behavior from chemistry can be applied.

Besides these, in practice a polarity index according to Snyder or Keller (Snyder, Principles of absorption chromatography, Decker, New York, 1968; Keller, Analytical chemistry, Weinheim, 1998, page 195) is used to classify solvents or solvent mixtures. Accordingly, polar solvents or solvent mixtures mean a solvent or solvent mixture with a polarity index of from 4 to 8, in particular from 5 to 7, preferably from 5.5 to 6.5, according to Snyder. Polar solvents are for example water, especially aqueous solutions. Polarly aprotic solvents are for example acetone, acetonitrile, ethyl acetate, dimethyl sulfoxide or N,N-dimethylformamide. Polarly protic solvents are for example alcohols which have an alkyl residue with 1 to 6 carbon atoms, for example methanol, ethanol, 1-propanol, 2-propanol (isopropanol), buthanol, pentanol or hexanol.

A nonpolar solvent or nonpolar solvent mixture means a solvent or solvent mixture which has a polarity index which is smaller by 0.3 or more than that of a reference solvent or reference solvent mixture. A polarity index smaller by 0.5 is preferred, in particular a polarity index smaller by 1, more preferably a polarity index smaller by more than 2. Consequently, the polarity index of the nonpolar solvent or solvent mixture has a value of from 5 to 1, in particular from 4 to 2, preferably from 3.5 to 2.5, according to Snyder. A 60% methanol/40% dichloromethane solvent mixture for example has a polarity index of 3.1 according to Snyder. Accordingly, suitable nonpolar solvents are for example halogenated solvents such as chloroform, dichloromethane or tetrachloromethane. Mention should also be made of aliphatic solvents such as pentane, hexane, heptane or cyclohexane. Besides these, aromatic solvents such as toluene or benzene should be mentioned as nonpolar solvents. Also suitable are ethers such diethyl ether, tert-butyl methyl ether or tetrahydrofuran.

In a further preferred embodiment of the method, the solvents are employed in the form of solvent mixtures, in particular in the form of solvent mixtures which comprise polar and nonpolar solvents.

The polar and nonpolar solvents are preferably employed in a ratio of 1:1, in particular in a ratio of 1:2, preferably in a ratio of 1:10 (polar/nonpolar).

This measure has the advantage that solvent mixtures can be prepared adapted to the characteristics of the biological materials. It is possible in this way to deal with a large number of separation problems.

In a further preferred embodiment of the method, surfactants, in particular nonionic surfactants, are also employed.

In a further preferred embodiment of the method, copolymers, especially copolymers of polyethylene oxides and polypropylene oxides, are employed as surfactants.

It has advantageously been found that gel formation is retarded by addition of surface-active substances, the so-called surfactants. As a result of the retardation of gel formation there is a longer interaction between the organic solvents and the biological materials undergoing gelation. The extraction of the ingredients is improved, especially the extraction of the lipophilic ingredients. The improved extraction of the ingredients, especially of the lipophilic ingredients, in the case of blood possibly derives from a displacement of the ingredients from cell membranes, in particular in the case of lipids on a displacement from protein bindings. The use of surfactants advantageously leads to an improvement in the spectroscopic properties of the ingredients of the supernatants to be investigated, preferably to an increased absorption of the ingredients.

The surfactants preferably used are those which are soluble in the solvent mixture, are free of toxic properties and/or have no influence on the analysis of the ingredients present in the supernatant. The measurability of absorption and/or fluorescence of the ingredients preferably remains unimpaired.

The surfactants are preferably employed in concentrations which preclude hemolysis of blood. The surfactants advantageously employed are copolymers, in particular copolymers of polyethylene oxides and polypropylene oxides. Suitable copolymer surfactants are for example commercially available Pluronic surfactants, preferably Pluronic 101.

In a further preferred embodiment, the biological materials are treated with the organic solvents in a ratio of 1:50, in particular in a ratio of 1:10, preferably in a ratio of 1:3.

It may, depending on the characteristics of the biological materials and extracting power of the organic solvents, be expedient to choose a larger or smaller ratio of biological materials to organic solvents, and this depends in particular on the subsequent analysis. The ratio is preferably chosen so that the limit of detection and limit of quantitation respectively in the analysis of the ingredients are taken into account.

In a further embodiment, the method is carried out at a temperature in the range from 5° C. to 60° C., in particular in the range from 10° C. to 40° C.

In a further embodiment, the method is carried out under a pressure between 0.5 bar to 5 bar, in particular between 0.8 bar to 2 bar.

The method can theoretically be carried out in temperature and/or pressure ranges with which gel formation is to expected. Besides this, account must be taken of solvent properties, especially melting point, boiling point, flash point. The method is carried out according to the invention at room temperature and atmospheric pressure.

In a further preferred embodiment of the method, the biological materials are treated for a period of from 10 seconds to 10 minutes, in particular from 10 seconds to 5 minutes, preferably from 10 seconds to 3 minutes, to extract the ingredients.

The consolidation of the biological materials advantageously takes place according to the invention in parallel with the extraction of the ingredients. The consolidation period can be controlled in a desired manner through the treatment of the biological materials with the solvent mixtures. The addition of gelators shortens the duration of extraction, and the addition of surfactants prolongs the duration of extraction. It has surprisingly been found that the biological materials, especially blood, preferably whole blood, are consolidated within a few minutes by the treatment according to the method of the invention. There is formation, purely through gravitational forces, of a consolidated sediment through the sinking of the biological materials to the bottom, and of a supernatant located above it. The supernatant can if required be simply removed. Ingredients of the biological materials which are dissolved in the supernatant are subjected to more detailed analysis. It is unnecessary to separate the biological materials from the extract by centrifugation and/or filtration. An advantageous result of the method carried out according to the invention is therefore a saving of time in the analysis.

The biological materials are preferably transferred, before the treatment with the organic solvents, into a solvent-resistant environment.

In a further preferred embodiment, the solvent-resistant environment used is a vessel with a hydrophobic surface, in particular a vessel with a surface made hydrophobic by silanization.

In a further embodiment, a vessel with a hydrophobic surface, in particular a plastics vessel, preferably made of polypropylene, is used.

It is advantageously possible in the method of the invention to use vessels with hydrophobic surfaces. The hydrophobic surfaces can be produced in the case of glass vessels by silanization of the glass surface or by etching with hydrogen fluoride. Besides these, it is also possible to use plastics vessels, preferably made of polypropylene, in the method of the invention. A use of composite materials for the vessels, in particular plastics-coated vessels, are also possible. The vessels preferably used have characteristics suitable for spectroscopic investigations.

In a further preferred embodiment of the method, the ingredients are converted into a lipophilic form and/or lipophilically modified before the extraction.

The supernatant is preferably investigated for lipophilic ingredients. The lipophilic ingredients may be present in the biological materials in bound form, especially in physically and/or chemically bound form. Besides these, it may be of interest to investigate ingredients with a lipophobic or hydrophilic nature.

The lipophilization of the ingredients is advantageously achieved by chemical and/or physical means. Enzyme-substrate reactions leading to defined products should be mentioned as lipophilization brought about chemically. Examples to be mentioned would be cleavage of fatty acid esters by lipases or reaction of lipophilically modified substrates by other enzymes. Thus, for example, a starch molecule coupled to a dye molecule such as Dabcyl-NHS ester is, despite the lipophilic dye, still soluble in water. The starch macromolecule is broken down stepwise into smaller units by the digestion caused by amylase. This results in the hydrophilic part decreasing in size and the overall molecule becoming more lipophilic until the dye molecule dominates the dissolving properties and transfers into the organic phase. A suitable lipophilization brought about physically is binding to lipophilic substances. For example, hydrophilic substances can bind to antibodies which, through their lipophilic parts, bring about a lipophilicity for such an overall complex. It is furthermore possible also to employ chelators as lipophilic molecules. For example, iron is transferred from blood into the organic phase through binding to a lipophilic chelator and can be analyzed there.

In a further embodiment of the method, at least one of the ingredients comprises carbohydrates, lipids, nucleic acids, proteins, macroelements, trace elements and/or vitamins.

Suitable carbohydrates are saccharides, especially polysaccharides, preferably monosaccharides. Suitable lipids are fatty acids, triglycerides (triacylglycerides, fatty acid esters of glycerol), glycerophospholipids such as phosphatidic acids, lecithins, cardiolipins, plasmalogens, etc.; sphingolipids such as sphingosines, ceramides, sphingophospho- and sphingoglycolipids; isoprenoids (terpenes) such as steroids, especially steroid derivatives, carotenoids, etc.; waxes (esters of long-chain aliphatic alcohols with fatty acids), and lipopolysaccharides (ingredients of the cell surface of Gram-negative bacteria). Suitable examples of vitamins are lipophilic vitamins, especially vitamin A, vitamin D, vitamin E and/or vitamin K. Besides these, also suitable as ingredients are provitamins, profactors and/or retinoids (vitamin A derivatives). The lipids are preferably triglycerides, fatty acids, cholesterols and/or carotenes, especially beta-carotene. Hormones should be mentioned in particular as ingredients which occur in a plurality of classes of substances.

In a further preferred embodiment of the method, the ingredients are secondary plant ingredients. Suitable secondary plant ingredients are alkaloids, flavonoids and/or carotenoids, especially xantophylls and/or carotenes, preferably beta-carotenes.

All of the ingredients of the biological materials which are accessible by the method of the invention can be subjected to subsequent analysis. This particularly includes derivatives of the ingredients mentioned above.

In a further preferred embodiment of the method, the ingredients are investigated by spectrometry, in particular colorimetry, preferably fluorimetry.

All known analytical techniques are suitable for the subsequent analysis of the ingredients. Separation of the ingredients, for example by chromatographic methods, in particular with high performance liquid chromatography (HPLC) may prove to be useful for the further analysis. The supernatant is expediently subjected to analytical methods which investigate the ingredients by spectrometry. Suitable spectrometric methods are those which investigate the ingredients by an interaction with electromagnetic radiation, for example NMR, IR, UV-vis, laser-Raman spectroscopy. Besides these, all known mass spectrometric methods can be used.

The present invention also solves the technical problem underlying it by a use of organic solvents or organic solvent mixtures for analyzing ingredients of biological materials, where the analysis is employed for the diagnosis and/or monitoring of therapy of disorders, especially of metabolic disorders and/or deficiency disorders.

Metabolic disorders and/or deficiency disorders generally lead to an excess or a deficiency, in particular a lack, of substances in the human and/or animal organism. Disorders may result therefrom. The present invention can be employed for diagnosing such disorders. A monitoring of therapy, in particular for analyzing pharmacological active ingredients used for therapy and/or nutrients, preferably for monitoring a supplementation of nutrients, can be carried out particularly advantageously with the present invention.

The ingredients are preferably substantially lipophilic substances.

The present invention also solves the technical problem underlying it by providing a spectrophotometer, in particular a hand photometer, for measuring ingredients of biological materials in a cylindrical vessel, with the ray path of the photometer being adjusted so that the measurement covers an upper half of the vessel.

In the context of the present invention, a cylindrical vessel means a vessel which has a profile which remains the same over its entire length. A suitable profile which remains the same is a rectangular cross section, in particular a square cross section, as used in spectroscopic cuvettes. The vessels used for measuring the ingredients of the biological materials are advantageously those in which the method of the invention was carried out. Analysis of the ingredients advantageously takes place after extraction without delay in the spectrophotometer of the invention.

It is to be stated in summary that the present invention makes it possible to extract ingredients from biological materials, and simplifies further analysis of the ingredients. The analysis of blood in particular is simplified thereby. Scarcely measurable variations in temperature occur while the method of the invention is being carried out, and no hemolysis of blood has been observed. In addition, elaborate separation steps such as filtration and/or centrifugation of the samples are unnecessary. The invention can be carried out in one step. It is therefore particularly suitable for miniaturized methods, in particular high-throughput methods which are known in the form of labs-on-a-chip and are preferably used in the so-called point of care systems.

Further features and advantages of the invention are evident from the following description of preferred embodiments by means of examples in conjunction with the dependent claims. In this connection, the individual features can each be implemented on its own or as a combination of a plurality with one another.

DETAILED DESCRIPTION OF THE EXEMPLARY EMBODIMENTS

The invention is described and explained in detail below by means of selected exemplary embodiments in connection with the appended drawings. These show:

FIG. 1 spectra contaminated by hemolysis in the ultraviolet-visible region (UV-vis spectrum) of beta-carotene from bovine serum, FIG. 2 a UV-vis spectrum comparable to FIG. 1 of beta-carotene from bovine serum, but free of hemolysis, FIG. 3 an HPLC chromatogram after an extraction according to the invention of carotenoids from human whole blood, FIG. 4 a tabular comparison of an extraction according to the invention of beta-carotene under the influence of an added surfactant, FIG. 5 solvent mixtures which have two solvents and their influence on a recovery I of beta-carotene, retinol and tocopherol, FIG. 6 solvent mixtures which have three solvents and their influence on the recovery II of beta-carotene, retinol and tocopherol, FIG. 7 a comparison of a serum extraction and of a whole blood extraction carried out according to the invention, FIG. 8 the recovery III of various ingredients with various ethanol:isopropanol solvent mixtures in the extraction, and FIG. 9 a consolidation of blood in a vessel with surface not hydrophobicized and vessels with hydrophobicized surfaces.

EXEMPLARY EMBODIMENTS

Extraction and Determination of Vitamin A, Vitamin E and Carotenoids from Whole Blood The cattle-, horse-, dog-, cat-, bat- or human-derived whole blood was initially made incoagulable with anticoagulants, preferably with ethylenediaminetetraacetate (EDTA). A sample of the whole blood was then put into a plastics tube (polypropylene, PP) or surface-treated (silanized) glass tube. The sample was then mixed with a mixture of organic solvents. A mixture of polar and nonpolar solvents (ethanol/isopropanol/isooctane; 1:4:10) was added, using a syringe or pipette, to the blood present in a vessel. A mixture obtained in this way was cautiously shaken intensely by hand for 10 seconds. The blood sample showed an increase in its viscosity. A phase separation then takes place by sedimentation for 5 minutes. After 2 to 3 minutes, shaking and leaving to stand was repeated. A gelatinous consolidation of the blood sample in the lower part of the tube developed. An organic phase formed as supernatant in the upper part of the tube. The organic phase essentially comprised isooctane and extracted ingredients from the blood. The organic phase had a yellowish color due to extracted carotenoids. The coloration in the sample was more intense depending on the concentration of the carotenoids. The supernatants were either directly measured in a spectrophotometer or initially removed by pipette, concentrated, taken up in a suitable solvent and then measured for example by high performance liquid chromatography (HPLC).

Extraction and Determination of Vitamin A, Vitamin E and Carotenoids from Serum

The test procedure as described was retained. Likewise the measurement of the supernatants.

Extraction and Determination of Vitamin A, Vitamin E and Carotenoids from Colostral Milk.

Bovine or human colostral milk was used as biological material. Test procedure and measurement were undertaken as indicated.

Extraction and Determination of Vitamin A, Vitamin E and Carotenoids from Liver Tissue Liver tissue was homogenized in buffers by means of Ultratorax treatment by known methods.

The fluid to viscous homogenate was employed as biological material; test procedure and measurement were undertaken as indicated.

Extraction and Detection of Cholesterol from Whole Blood, Serum, Colostral Milk or Liver Tissue Lipophilic ingredients were initially extracted into the organic supernatant as described in the preceding examples. Cholesterol was then determined in an aliquot of the organic extract by means of known enzymatic methods.

Extraction and Detection of Nonesterified Fatty Acids (NEFA) from Whole Blood, Serum or Colostral Milk The lipophilic ingredients were initially extracted into the organic supernatant as described in the preceding examples. The NEFA were initially complexed with copper, and subsequently such a fatty acid-copper complex was detected by a color reaction. The color reaction was measured in a spectrophotometer. All the steps are advantageously carried out in the same extraction tube in the method. The copper reagent used was a mixture of copper-triethanolamine solution 1M TEA, 1N acetic acid, 6.45% $Cu(NO_3)_2$; 9:1:10 v/v). The copper reagent is added to the organic supernatant after a distinct consolidation of the whole blood has occurred. Intensely shaking for 20 seconds and an incubation time of about 30 minutes were followed by addition to the supernatant of a color reagent (0.5% solution of diphenylcarbazone and diphenylcarbazide (5:95%) or a 0.5% strength solution of diphenylcarbazone in methanol) and shaking. The color change was measured in a spectrophotometer at 550 nm.

Detection of Lipase Activity

To detect lipase activity in whole blood or serum, whole blood samples or serum samples were initially supplied with substrate. The substrate used was a fatty acid ester with a fluorescent fatty acid, which was emulsified in bile acid. Lipase present in the sample cleaves the substrate. Incubation of the sample is followed by extraction thereof with one of the solvent mixtures described, and measurement of the liberated labeled fatty acids. The signal intensity is proportional to the concentration of the enzyme in the blood.

DESCRIPTION OF THE FIGURES

FIG. 1 shows a diagram in which five different UV-vis spectra of beta-carotene extracts from bovine serum samples (BS73, BS75, BS76, BS79, BS80) in the wavelength range from 360 nm to 580 nm are depicted with their absorptions. Prior art methods were used to remove blood cells from the blood samples and to obtain blood sera. beta-Carotene was measured directly in the blood sera. Characteristic bands for beta-carotene normally at 450 nm and 480 nm plus a slight shoulder at 425 nm are expected in such extracts. All the samples gave spectra impaired by hemolysis of erythrocytes. It was found that the characteristic bands were shifted to larger wavelengths. Three of the samples were so heavily contaminated by the hemolysis that evaluation was impossible because of strong serum colorations.

FIG. 2 shows further five UV-vis spectra of beta-carotene. The beta-carotene was obtained from the bovine blood described in FIG. 1, but the extraction from whole blood was carried out by a method of the invention. Only the spectrum typical of beta-carotene was now to be seen in all the samples.

FIG. 3 shows an HPLC chromatogram of an extract obtained by the method of the invention. The extract of carotenoids was obtained from human whole blood. Absorption units were plotted against the retention time in minutes. Signals, called "peaks", were obtained for 1=lutein, 2=zeaxanthin, 3=canthaxanthin, 4=beta-cryptoxanthin, 5=alpha-carotene and 13-cis-beta-carotene, 6=beta-carotene, 7=9-cis-beta-carotene, 8 and 9=isomeric cis forms of lycopene and for 10=trans-lycopene. The signals are virtually symmetrical, i.e. virtually free of so-called signal tailing (peak tailing), and in some cases baseline-separated.

FIG. 4

FIG. 4 shows a table indicating a profile of beta-carotene concentrations as a function of various surfactant additions. The surfactant employed was Pluronic 101 in various concentrations (0.1%-3.0%). The surfactant was added in the stated concentrations to aliquots of two different bovine blood samples. The absorptions of beta-carotene were determined by spectrophotometry, and beta-carotene concentrations are calculated as mean±standard deviation in mg/l. An increase in the surfactant concentration led in both blood samples to an increase in the beta-carotene concentrations in the extracts.

FIG. 5 shows results of experiments on the recovery of alpha-tocopherol (vitamin E), retinol (vitamin A) and beta-carotene. Bovine whole blood was aliquoted in four parts and extracted by the method of the invention. Each aliquot comprised 250 μl. The following solvent mixtures were used for the extraction in the stated volumetric ratio: 1=ethanol/isooctane (1:2 V/V), 2=methanol/isooctane (1:2 V/V), 3=ethyl acetate/isooctane (1:2 V/V), 4=isopropanol/isooctane (1:2 V/V). HPLC was used as standard analysis. Retinol was determined as analyte with a recovery which was a minimum of 65% in the methanol/isooctane mixture and a maximum of 88% in the isopropanol/isooctane mixture. alpha-Tocopherol was recovered with a minimum of 21% in the ethyl acetate/isooctane mixture and with a maximum of 107% isopropanol/isooctane mixture. The recovery determined for beta-carotene in solvent mixtures 1 to 3 was worse than for the other analytes, with a minimum of 13% and maximum of 40%. Optimal recovery was found for all the analytes in the isopropanol/isooctane mixture.

FIG. 6 shows results of experiments on the recovery of alpha-tocopherol (vitamin E), retinol (vitamin A) and beta-carotene. The recovery was carried out as indicated in the description for FIG. 5. Solvent mixtures 5 to 11 were used: 5=ethanol/isopropanol/isooctane (1:1:4; V/V), 6=methanol/isopropanol/isooctane (1:1:4; V/V), 7=ethyl acetate/isopropanol/isooctane (1:1:4; V/V), 8=water/isopropanol/isooctane (1:1:4; V/V), 9=sodium chloride solution (0.9%)/ethanol/isopropanol/isooctane (1:1:4; V/V), 10=n-butanol/isopropanol/isooctane (1:1:4; V/V), 11=isopropanol/isooctane (2:4; V/V). Solvent mixtures 5 to 10 were employed for comparison with solvent mixture 11, which corresponds to solvent mixture 4 from FIG. 5, but in twice the amount here. Additionally, various protic solvents such as alcohols, water, saline solution were added to the "basic isopropanol/isooctane solvent mixture. It emerged that alpha-tocopherol and beta-carotene both showed comparable decreases and increases in their recovery in solvent mixtures 5 to 10. Besides the isopropanol/isooctane solvent mixture which was optimal for all analytes, the ethanol/isopropanol/isooctane mixture also showed high recoveries for all analytes.

FIG. 7 shows a comparison of extraction results between the conventional extraction of serum with the extraction by the method of the invention from whole blood. The analyte investigated was beta-carotene in 10 different blood samples from cows. The recovery of the analyte in the method of the invention is virtually identical to the classical method for all the blood samples.

FIG. 8 examines an influence of the solvent ratio of ethanol to isopropanol in the ethanol/isopropanol/isooctane solvent mixture on the extraction of the analytes alpha-tocopherol (vitamin E), retinol (vitamin A) and beta-carotene. Legend data relate to a content of the respective polar solvent in μl. 1 μl was used as the content of the nonpolar solvent isooctane. 250 μl of a bovine whole blood sample were employed.

FIG. 9 shows an influence of vessel surfaces on an adhesion of the blood cells and the result of the consolidation. FIG. 9A shows the extraction in a vessel with untreated surface, and FIG. 9B in a vessel with a surface hydrophobicized by silanization. The complete consolidation of the blood cells after about 10 minutes by turn over of the tube is demonstrated in FIG. 9C.

Figure 1:
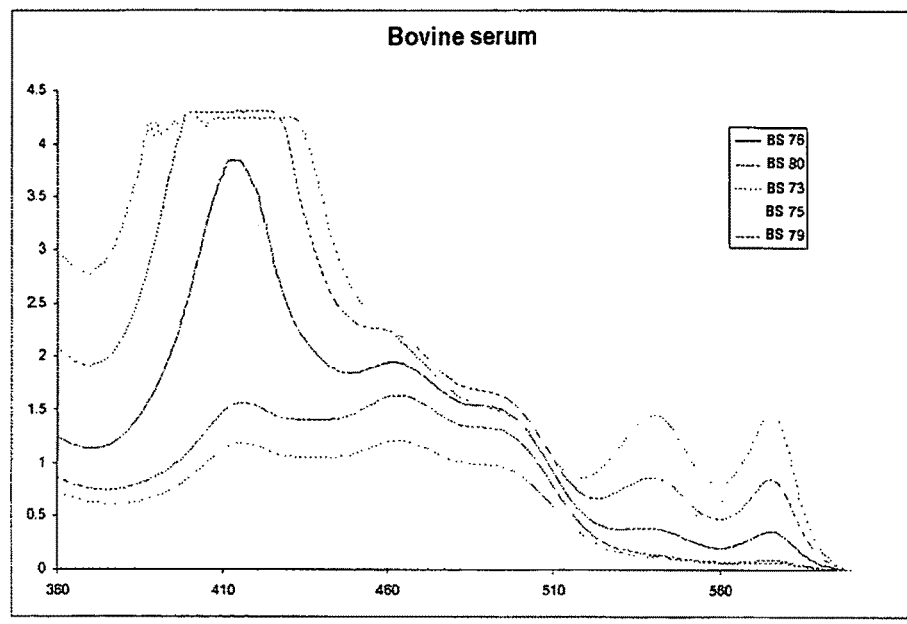
FIG. 1
Figure 2:
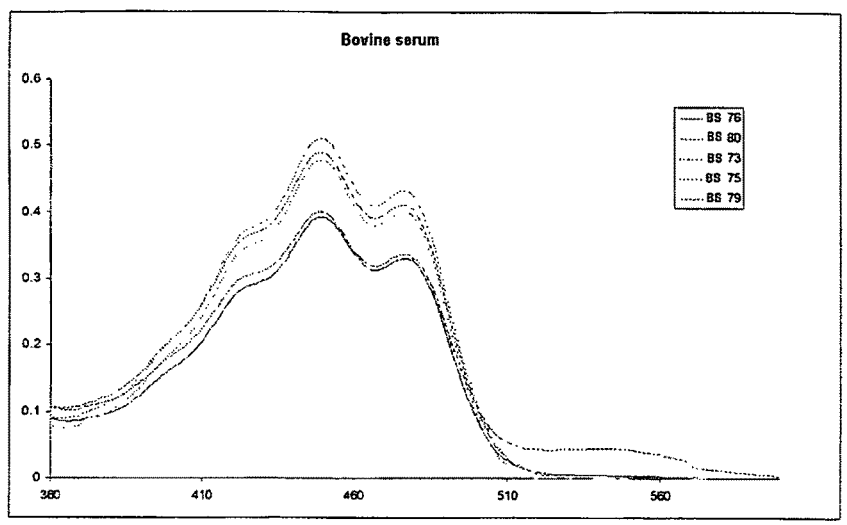
FIG. 2
Figure 3:
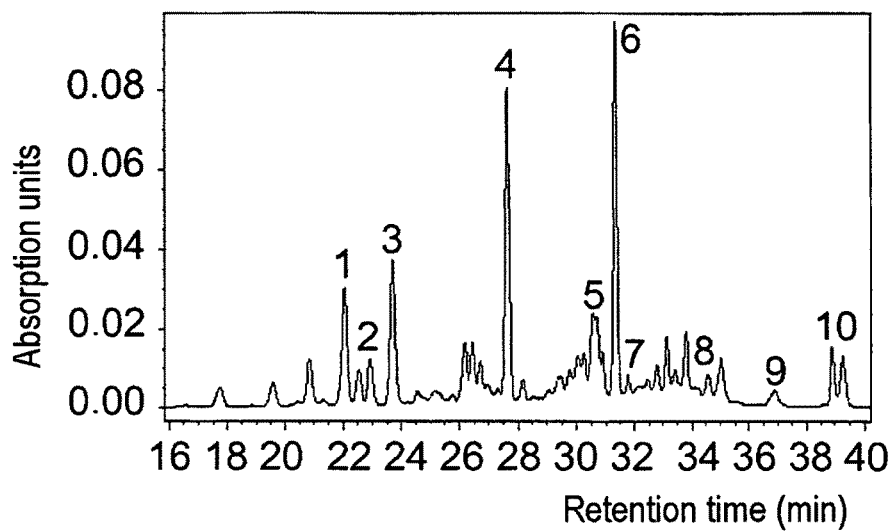
FIG. 3
Figure 5:
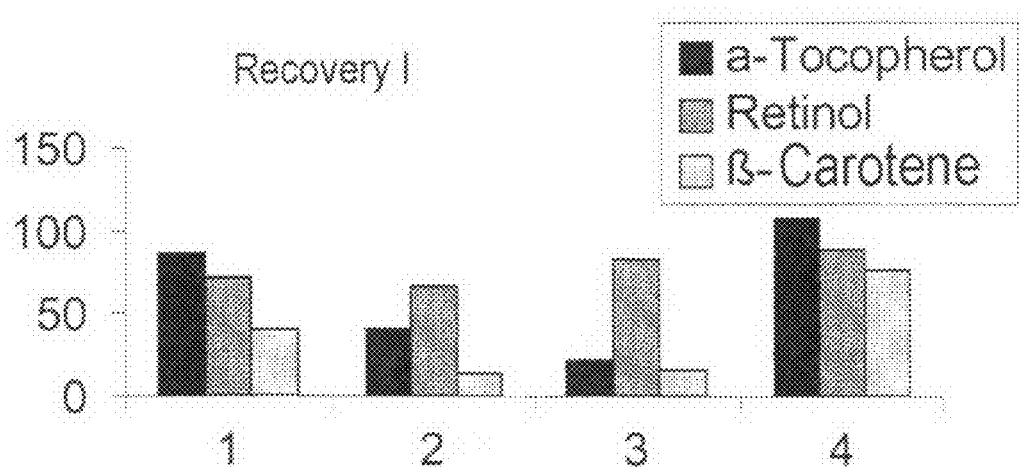
FIG. 5
Figure 6:
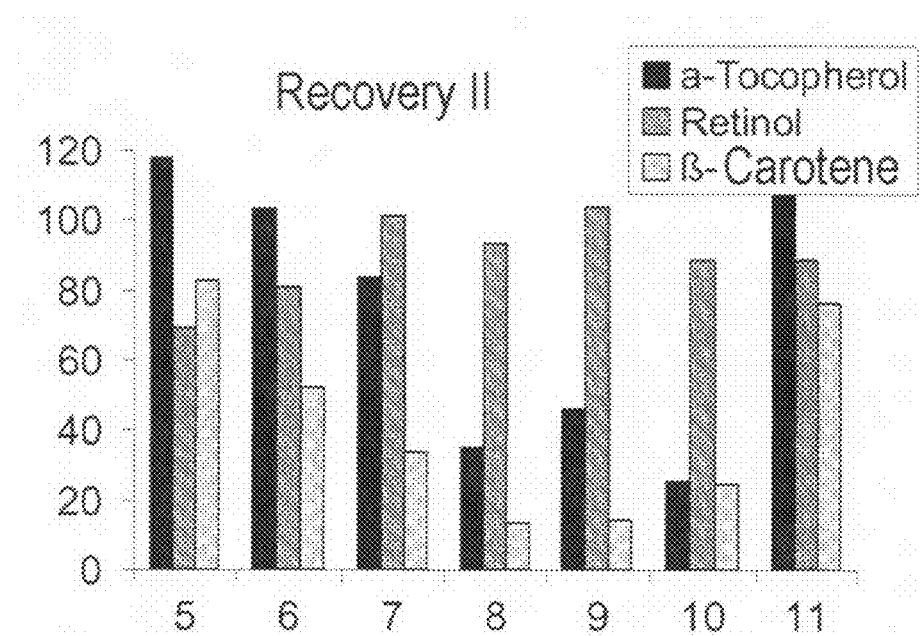
FIG. 6
Figure 7:
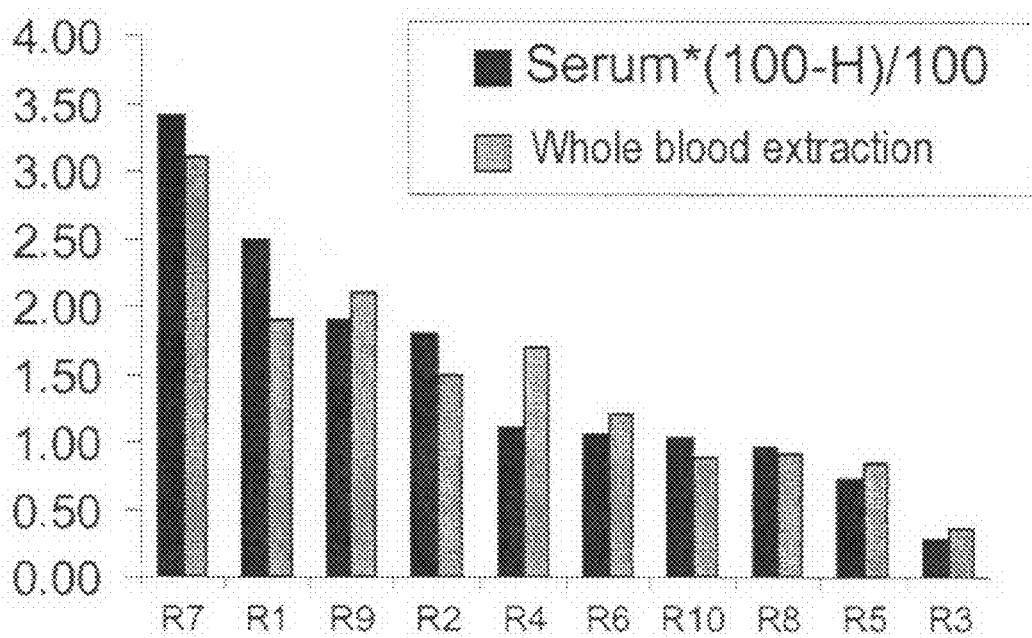
FIG. 7
Figure 8:
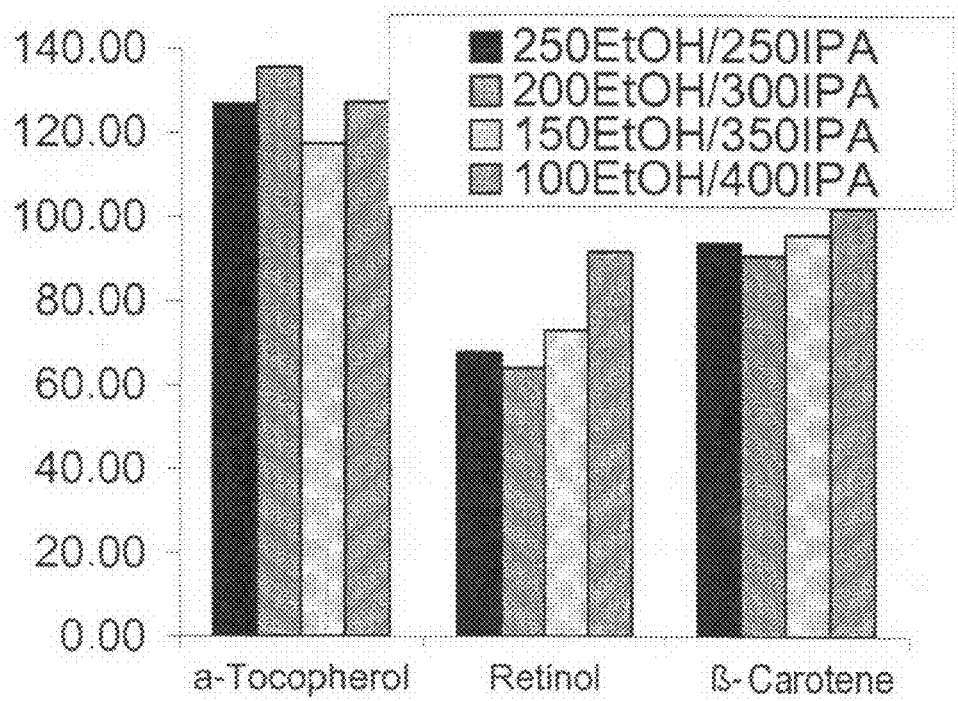
FIG. 8
Figure 9:
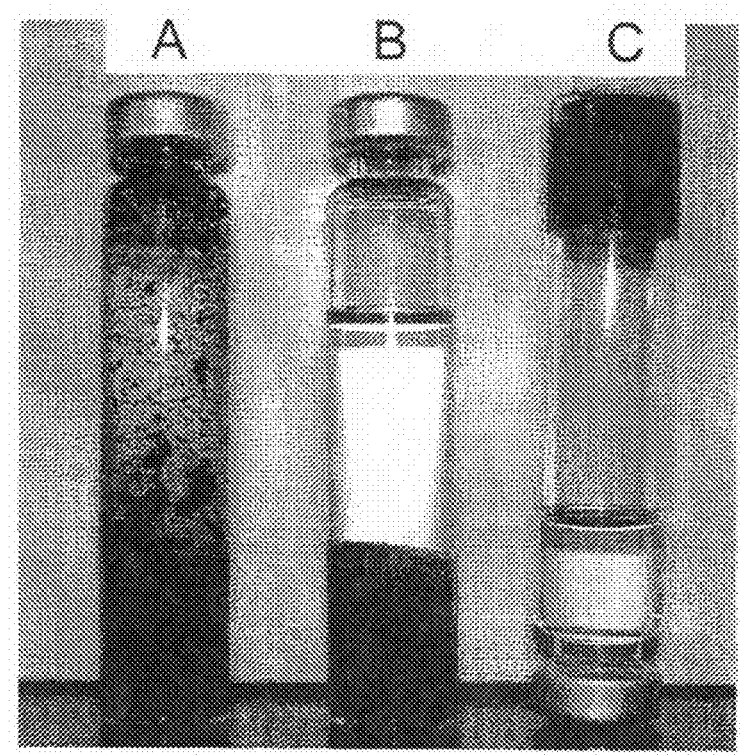
FIG. 9

The recovery of the individual analytes was on average 106% for alpha-tocopherol (vitamin E), 89% for retinol (vitamin A) and 95% for beta-carotene in blood samples from cows and horses.

The invention claimed is:

1. A method for analyzing whole blood, without centrifugation, comprising:
 a) placing whole blood in a vessel suitable for spectroscopic investigations, wherein an internal surface of said vessel in direct contact with said whole blood is hydrophobic, and wherein said whole blood is unfiltered and uncentrifuged;
 b) treating, in said vessel, said whole blood in one step with at least one organic solvent mixture comprising at least one polar organic solvent and at least one nonpolar organic solvent, so that said organic solvent mixture extracts the whole blood, producing a consolidated sediment and a supernatant of liquid organic phase; and
 c) performing a direct spectrometric and/or fluorimetric analysis on said supernatant within said vessel, wherein said supernatant is continuously present in said vessel prior to and during said analysis.

2. The method of claim 1, wherein said polar organic solvent is a polar protic solvent.

3. The method of claim 2, wherein said polar protic solvent is selected from the group consisting of methanol, ethanol, 1-propanol, 2-propanol (isopropanol), butanol, pentanol, hexanol and mixtures thereof.

4. The method of claim 1, wherein said nonpolar solvent is an alkane.

5. The method of claim 4, wherein said alkane is selected from the group consisting of hexane, heptane, octane and mixtures thereof.

6. The method of claim 1, wherein at least one surfactant is added to said whole blood.

7. The method of claim 1, wherein at least one surfactant is added to said organic solvent mixture.

8. The method of claim 6, wherein said surfactant is a copolymer.

9. The method of claim 7, wherein said surfactant is a copolymer.

10. The method of claim 1, wherein a ratio of said whole blood and said organic solvent mixture is 1:3 (one part whole blood to three parts organic solvent mixture).

11. The method of claim 1, wherein said method is performed at a temperature range from 5° C. to 60° C.

12. The method of claim 1, wherein said method is performed under a pressure in the range from 0.5 bar to 5 bar.

13. The method of claim 1, wherein an extraction time of said whole blood in step (b) is between 10 seconds and 10 minutes.

14. The method of claim 1, further comprising a step of converting said whole blood into a lipophiliclly modified form before extraction.

15. The method of claim 14, wherein before extraction, water soluble ingredients of said whole blood form a lipophilic complex with a lipophilic molecule.

16. The method of claim 14, wherein before extraction, water soluble ingredients of said whole blood form a lipophilic complex with a lipophiliclly modified molecule.

17. The method of claim 14, wherein said step of converting said whole blood into said lipophiliclly modified form is performed enzymatically.

18. The method of claim 1, wherein said whole blood comprises ingredients which are selected from the group consisting of carbohydrates, lipids, nucleic acids, proteins, macroelements, trace elements, vitamins and mixtures thereof.

19. The method of claim 18, wherein said lipids are selected from the group consisting of triglycerides, fatty acids, cholesterols, carotenes and mixtures thereof.

20. The method of claim 1, wherein said vessel is made of glass, which is made hydrophobic by silanization.

21. The method of claim 1, wherein said vessel is made of glass, which is made hydrophobic by etching with hydrogen fluoride.

22. The method of claim 1, wherein said vessel is made of plastic.

23. The method of claim 22, wherein said vessel is made of polypropylene.

\* \* \* \* \*